United States Patent [19]

Soled et al.

[11] Patent Number: 5,208,200

[45] Date of Patent: May 4, 1993

[54] NOBLE METAL ON RARE EARTH MODIFIED SILICA ALUMINA AS HYDROCARBON CONVERSION CATALYST

[75] Inventors: Stuart L. Soled, Pittstown; Gary B. McVicker, Califon; William E. Gates, Somerset, all of N.J.

[73] Assignee: Exxon Research and Engineering Co., Florham Park, N.J.

[21] Appl. No.: 842,863

[22] Filed: Feb. 27, 1992

[51] Int. Cl.$^5$ ............................ B01J 21/12; B01J 23/10
[52] U.S. Cl. ............................ 502/241; 502/242; 502/261; 502/263
[58] Field of Search ............... 502/261, 263, 235, 241, 502/242

[56] References Cited

U.S. PATENT DOCUMENTS

| | | | |
|---|---|---|---|
| 2,882,245 | 4/1959 | Heinemann et al. | 502/261 |
| 2,976,232 | 3/1961 | Porter, Jr. et al. | 208/138 |
| 3,002,921 | 10/1961 | Gladrow et al. | 208/138 |
| 3,223,617 | 12/1965 | Maziuk | 208/138 |
| 3,247,099 | 4/1966 | Oleck et al. | 208/138 |
| 3,649,524 | 3/1972 | Derr et al. | 208/139 |
| 3,776,860 | 12/1973 | Rai | 252/455 R |
| 3,836,594 | 9/1974 | Sampson et al. | 502/263 |
| 4,024,077 | 5/1977 | Engelhard et al. | 252/442 |
| 4,039,477 | 8/1977 | Engelhard et al. | 208/139 |
| 4,218,308 | 8/1980 | Itoh et al. | 502/261 |
| 4,227,993 | 10/1980 | Engelhard et al. | 208/139 |

FOREIGN PATENT DOCUMENTS

| | | |
|---|---|---|
| 1243366 | 10/1968 | United Kingdom . |
| 1390625 | 11/1971 | United Kingdom . |
| 2121698 | 1/1984 | United Kingdom ........ 502/263 |
| 2166970 | 5/1986 | United Kingdom ........ 502/235 |

OTHER PUBLICATIONS

Sinfelt, J. H., Bifunctional Catalysis, Academic Press 1964, vol. 5 pp. 37–74, *Advances in Chemical Engineering*.

*Primary Examiner*—Carl F. Dees
*Attorney, Agent, or Firm*—Estelle C. Bakun

[57] ABSTRACT

Rare earth oxides, such as $Nd_2O_3$ disperse onto the surface of $SiO_2/Al_2O_3$ and act as weakly basic titrants. This lowers the acidity of $SiO_2/Al_2O_3$ to close to that of chlorided alumina, as shown by model compound reaction tests. This support also disperses a noble metal such as Pt much better than undoped $SiO_2/Al_2O_3$ and similar to chlorided alumina. Platinum on the rare earth modified silica alumina can function as a hydrocarbon conversion catalyst in reactions where Pt/chlorided $Al_2O_3$ is used, such as in reforming, and isomerization, especially wax isomerization.

8 Claims, 4 Drawing Sheets

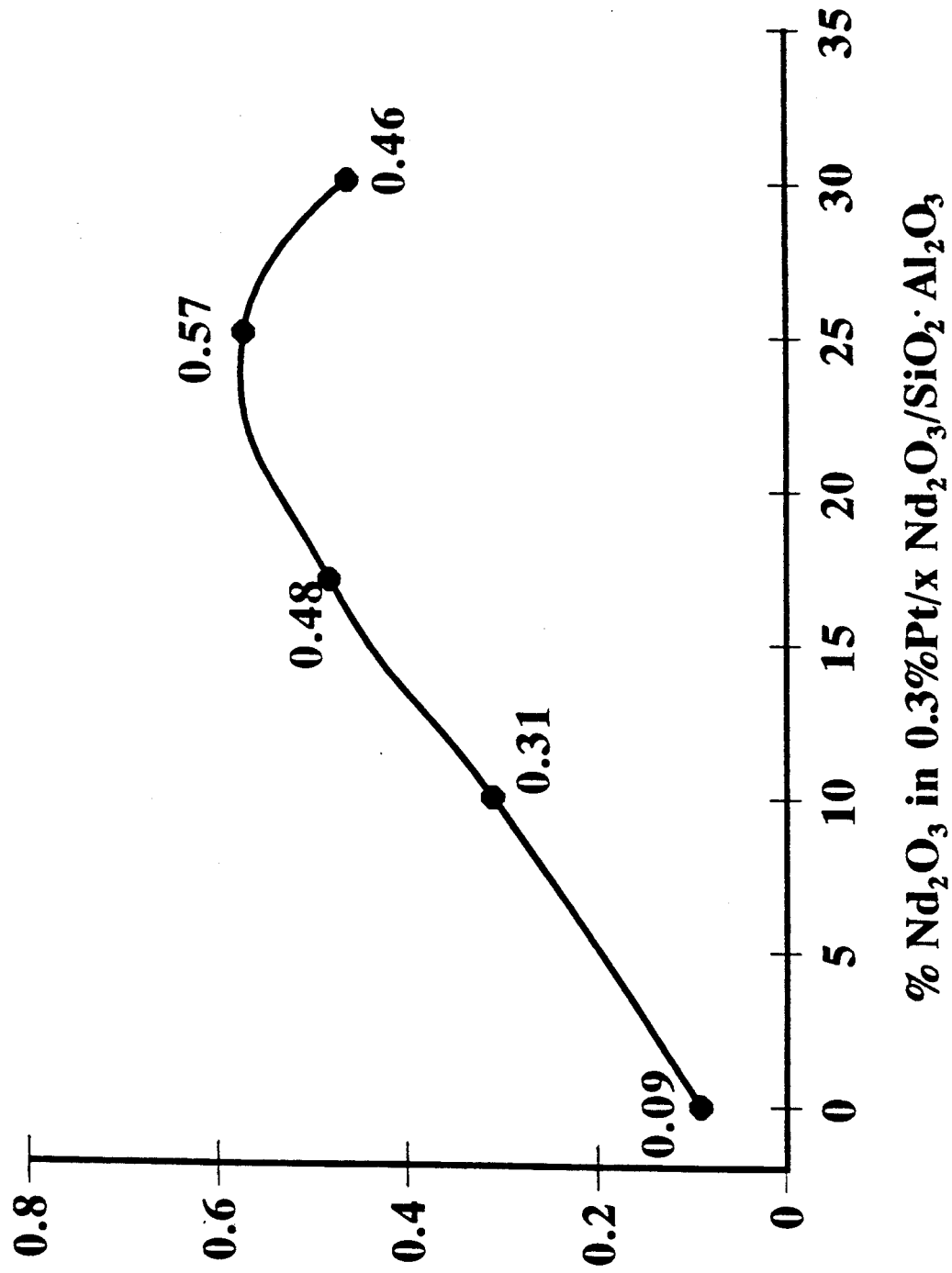

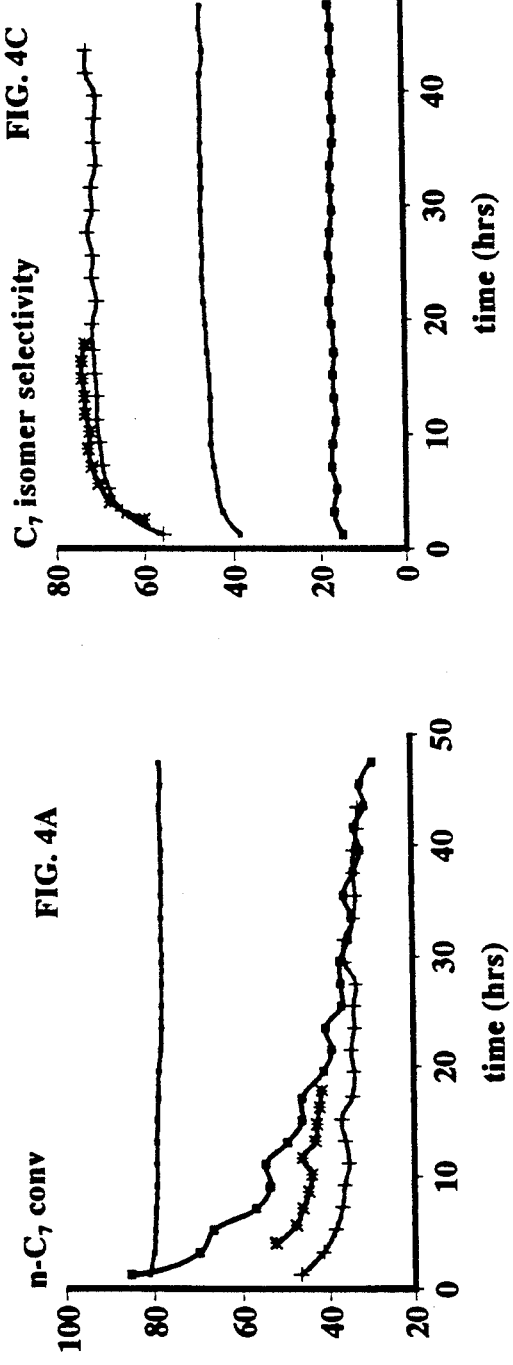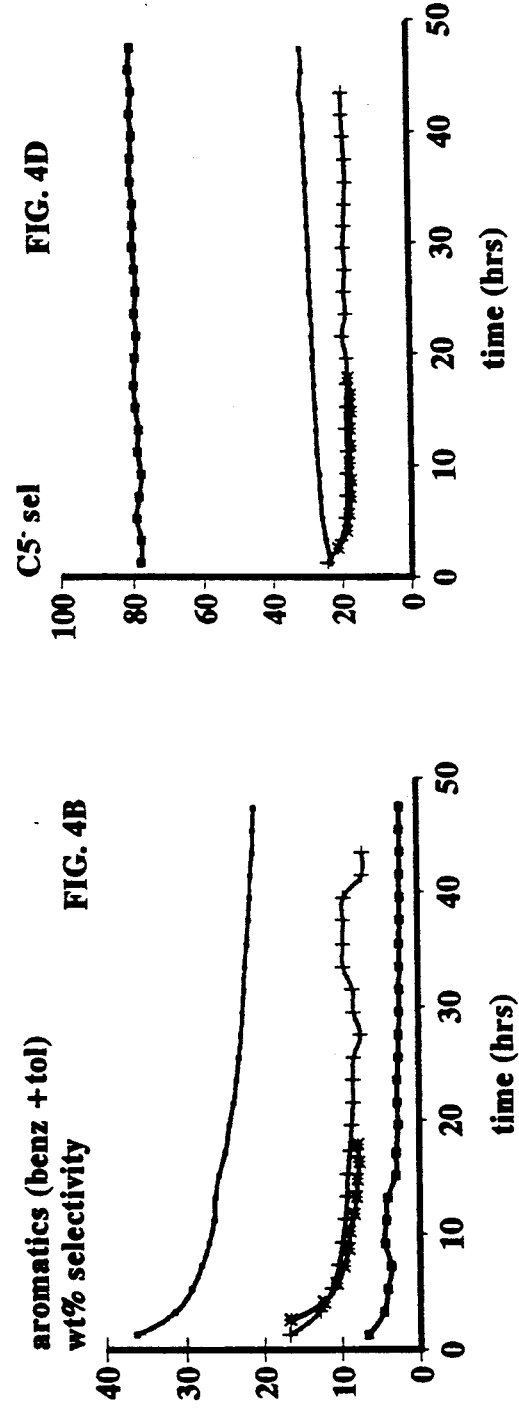

NOBLE METAL ON RARE EARTH MODIFIED SILICA ALUMINA AS HYDROCARBON CONVERSION CATALYST

FIELD OF THE INVENTION

Applicants have discovered that a rare earth oxide dispersed onto the surface of amorphous silica-alumina can act as a weakly basic titrant lowering the acidity of the amorphous silica-alumina to near that of halided-alumina. Surprisingly, this support disperses a supported noble metal phase much better than unmodified silica-alumina, and to the same extent as halided-alumina. Platinum on rare earth modified amorphous silica-alumina can be utilized as a hydrocarbon conversion catalyst in reforming reactions typically employing platinum on chlorided-alumina catalysts. The necessity of chlorine addition during reforming, required for chlorided-alumina catalysts, which is both inconvenient and environmentally detrimental, is removed. Additionally, the rare earth oxide modified amorphous silica-alumina catalyst provides permanent acidity, unlike chlorided alumina catalysts whose acidity decreases as chlorine is depleted during use of the catalyst, thereby lowering activity and requiring chlorine addition to maintain acidity.

In addition to performing as bifunctional reforming catalysts, the noble metal-loaded rare earth modified amorphous silica-alumina catalysts are capable of being used in isomerization reactions, especially wax isomerization reactions.

SUMMARY

By this invention there is provided a catalyst composition comprising an amorphous silica-alumina support having dispersed thereon a rare earth oxide, which as herein used includes yttrium oxide, and further impregnated with metal(s) selected from the group consisting of Group VIII noble metal(s), mixtures of Group VIII noble metal(s) and tin, and mixtures of Group VIII noble metal(s) and rhenium. The amorphous silica-alumina support contains at least about 50% silica by weight. As used herein amorphous means noncrystalline as indicated by x ray diffraction (no presence of sharp reflections).

The invention is also directed to a method of using such catalyst in hydrocarbon conversion reactions such as reforming reactions and isomerization reactions, especially wax isomerization reactions.

BRIEF DESCRIPTION OF DRAWINGS

FIG. 3 depicts the enhancement of platinum dispersion as a function of rare earth oxide addition to amorphous silica-alumina by measuring the H atoms absorbed per Pt metal atom (H/M) using the $H_2$ chemisorption technique.

FIG. 4 views A, B, C, and D compare present invention catalysts and a platinum chlorided-alumina catalyst containing 0.3% platinum and 0.9% Cl and a Pt silica-alumina catalyst containing 0.6% platinum in a reforming reaction for n-$C_7$ conversion, aromatics selectivity, $C_7$ isomer selectivity, and $C_5$- selectivity respectively.

DETAILED DESCRIPTION OF INVENTION

Figure 1:
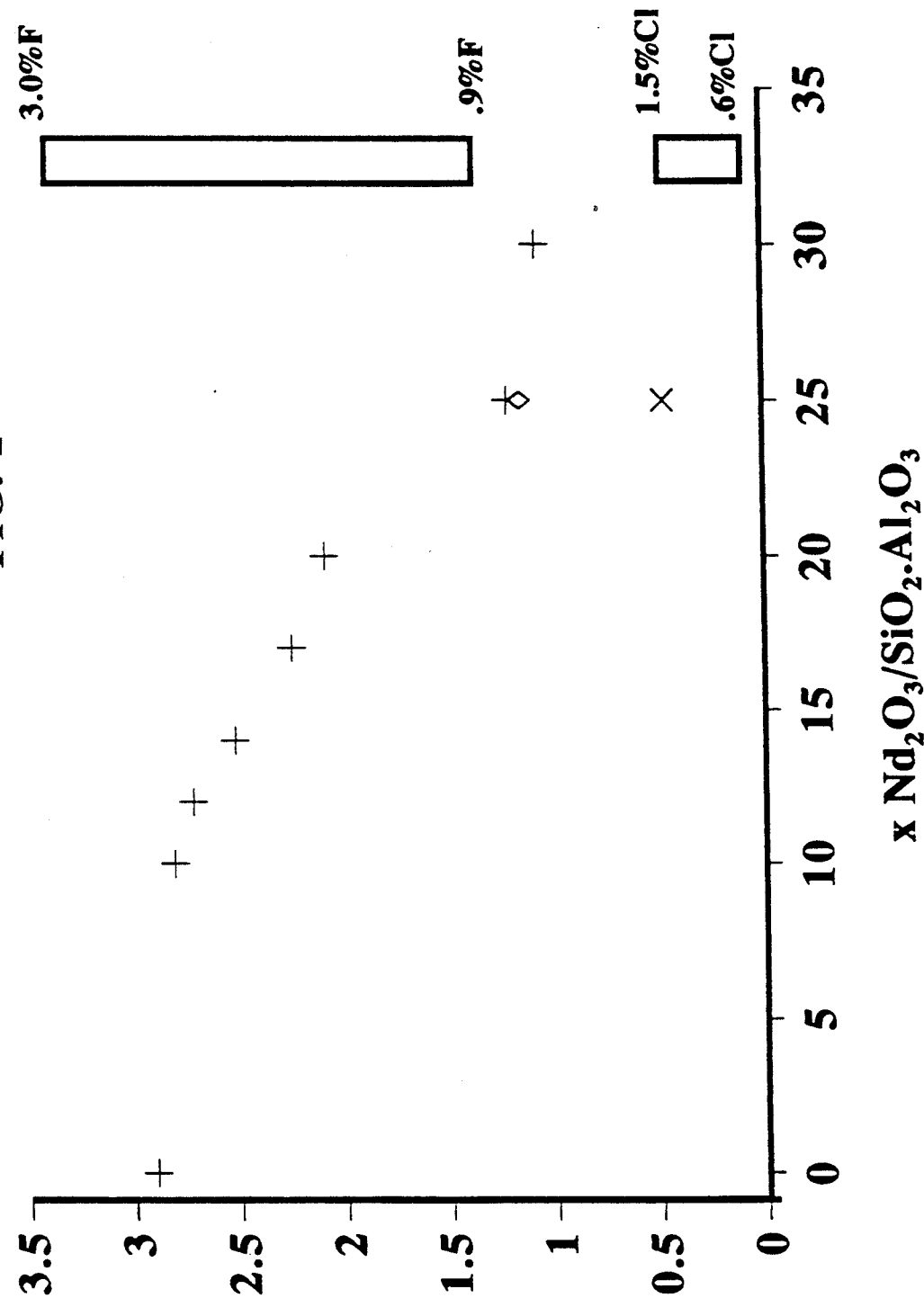
FIG. 1 graphically compares the acidity of rare earth modified amorphous silica-alumina as a function of rare earth oxide loading with the acidity of chlorided and fluorided alumina. The comparison is accomplished by using the 2-methylpent-2ene acidity probe test and measuring the ratio of 3-methylpent-2ene to 4-methylpent-2ene (refer to Example 1).

The present invention utilizes a weakly basic rare earth oxide to decrease the acidity of an amorphous silica-alumina support to near that of halided-alumina catalysts. Thus, the support, having platinum dispersed thereon, can function as a hydrocarbon conversion catalyst in reactions where Pt/chlorided $Al_2O_3$ is used, for example, in reforming.

The amorphous silica-alumina support of the present catalyst may be prepared by any of a number of conventional methods known to those skilled in the art. Alternatively, the amorphous silica-alumina support may be purchased from commercial sources. The support of the instant catalyst has a silica to alumina ratio of between about 95:5 & 50:50, preferably 75:25 $SiO_2:Al_2O_3$.

Prior to modification by addition of a rare earth oxide, the amorphous silica-alumina support is calcined in air at a temperature ranging from about 400° to about 600° C. The support is then impregnated with an aqueous solution of a rare earth salt which upon calcination is converted to a rare earth oxide. The rare earths are those elements of the periodic table having atomic numbers 57 to 71. Also included is yttrium, having an atomic number of 39, which behaves similar to rare earths in many applications. Suitable rare earths include, for example, neodymium, gadolinium and samarium with neodymium and yttrium being preferred. Mixtures of rare earth oxides may also be used. The amount of rare earth oxide impregnated onto the silica-alumina support ranges from about 1 wt% to about 90 wt%, preferably 10 wt% to about 25 wt%. Typically, the rare earth oxide is added to the support in the form of a hydrated salt, e.g. $Nd(NO_3)_3.6H_2O$. The impregnation is accomplished via the incipient wetness technique, however, other techniques known to those skilled in the art are also suitable. The impregnated support is then dried at about 100° to about 150° C. and calcined between about 300° and about 900° C., preferably about 400° to about 600° C. for about 1 to about 24 hours, preferably about 4 hours. Calcination converts the hydrated salt to the rare earth oxide.

A metal selected from the group consisting of Group VIII noble metal(s), mixtures of Group VIII noble metal(s) and rhenium, and mixtures of Group VIII noble metal(s) and tin, is then impregnated onto the rare earth oxide modified amorphous silica-alumina support to provide hydrogenation-dehydrogenation functions, preferably platinum is employed. Preferably, the Group VIII noble metal(s) will be present on the catalyst in an amount from about 0.01 to about 10 wt%, calculated on an elemental basis, of the final catalyst composition. More preferably, the catalyst contains from about 0.01 to about 2.0 wt% platinum, most preferably about 0.3 to 0.6 wt% platinum. The catalyst of the present invention may also contain promoters or other metals that may be used in conjunction with, e.g. platinum, in reforming or isomerization, especially wax isomerization, such as iridium, rhenium, palladium, ruthenium, rhodium and mixtures thereof in concentrations ranging from about 0.01 to 10 wt%, preferably from about 0.01 to 2.0 wt%, more preferably from about 0.3 to 0.6 wt%. When Group VIII noble metal(s) is employed, tin may also be present in concentrations ranging from about 0.01 to 10 wt%, preferably from about 0.01 to 2.0 wt%, more preferably from about 0.3 to 0.6 wt%. Preferably tin will be present with platinum.

The metals can be incorporated onto the rare earth oxide modified support via the incipient wetness, or other suitable technique known to those skilled in the art. An absorption technique from a dilute or concentrated solution, with subsequent filtration or evaporation to effect the uptake of the metallic component, may also be used. The solution used in impregnating the catalyst e.g. can be a salt or acid solution having the respective Group VIII noble metal(s), and rhenium or tin dissolved therein. The impregnation can be carried out under a variety of conditions known to those skilled in the art including ambient and elevated temperatures, and atmospheric and superatmospheric conditions.

The catalyst after impregnation of the Group VIII noble metal, is dried by heating at a temperature above about 27° C., preferably between about 65° C. and 150° C., in the presence of nitrogen, oxygen, or both, in an air stream or under vacuum. It is then calcined at a temperature from about 300° C. to 650° C., preferably 400° C. to 560° C., in the presence of nitrogen or oxygen in an air stream, or in the presence of a mixture of oxygen and an inert gas. This calcination, or activation, is conducted for periods ranging from about 1 to about 24 hours in either flowing or static gases.

The catalyst of the present invention can be contacted with a feedstream comprising $C_5+$. When utilized in a reforming process the feedstream will preferably be $C_5$ to C 200° C. hydrocarbons, in an isomerization reaction using a liquid feedstream, the feedstream will preferably be normal $C_5$ to $C_9$ paraffins. When the wax isomerization reaction is performed, the feed will preferably be $C_{12}+$ hydrocarbons.

In a catalytic reforming process, a hydrotreated naphtha stream comprising $C_5+$, preferably $C_5$ to C 200° C. hydrocarbons, that typically contains about 20-80 volume % paraffins, 20-80 volume % naphthenes, and about 5-20 volume % aromatics, and boiling at atmospheric pressure between about 27° and 232° C., preferably between about 66° and 191° C., is brought into contact with the catalyst system of the present invention in the presence of hydrogen. The reaction typically takes place in the vapor phase at a temperature ranging from about 350° to 550° C., preferably about 400° to 530° C. Reaction zone pressures may range from about 1 to 50 atmospheres, preferably from about 5 to 25 atmospheres.

The naphtha feedstream is generally passed over the catalyst at space velocities ranging from about 0.5 to 20 parts by weight of naphtha per hour per part by weight of catalyst (w/hr/w), preferably from about 1 to 10 w/hr/w. The hydrogen to hydrocarbon mole ratio within the reaction zone is maintained between about 0.5 and 20, preferably between and 10. During the reforming process, the hydrogen employed can be in admixture with light gaseous hydrocarbons. Since the hydroforming process produces large quantities of hydrogen, a recycle stream is employed for admission of hydrogen with the feed.

The wax which may be isomerized using the catalyst of the present invention is any readily available natural or synthetic wax. Natural waxes include those waxes obtained by dewaxing natural hydrocarbons, commonly called slack waxes. Slack waxes contain anywhere from 0 to 45% oil or more depending on the molecular weight of the oil being dewaxed to a particular point. It is preferred that when slack wax is used as the isomerization feed, it will contain from about 1 to about 35 wt% oil, preferably about 1-25 wt% oil, more preferably 5-15 wt% oil, most preferably 7-10 wt% oil.

Slack waxes, coming from natural petroleum sources, contain numerous molecular species such as heteroatom compounds and polynuclear aromatic materials which are detrimental to the life and activity of isomerization catalysts. Thus, the heteroatoms should be removed prior to isomerization using a hydrotreating catalyst under mild hydrotreating conditions. Exemplary of hydrotreating catalysts are Ni/Mo on alumina and Co/Mo on alumina. Hydrotreating conditions are 250° C.–400° C.; 0.1–10 LHSV; 500 to 3000 psi $H_2$; 500–2000 SCF $H_2$/bbl. Following hydrotreating, acceptable levels will be a nitrogen content of about 1–5 ppm, preferably 2 ppm and less and a sulfur content of about 1–20 ppm, preferably 5 ppm and less.

The wax which may be isomerized using the catalyst of the present invention also includes Fischer-Tropsch Wax. Fischer-Tropsch Wax may be made as a by-product from the conversion of natural gas under known conditions to synthesis gas ($CO+H_2$) which may then be converted by the Fischer-Tropsch process to form gaseous and liquid hydrocarbons and a normally solid paraffin wax known as Fischer-Tropsch Wax. This wax does not contain the sulfur, nitrogen, or metal impurities normally found in crude oil, but it is known to contain water and a number of oxygenate compounds such as alcohols, ketones, aldehydes, etc.

Isomerization, especially wax isomerization, over the catalyst of the present invention can be conducted at a temperature of 250° to 400° C., 100 to 3000 psi $H_2$; 500 to 10000 SCF/bbl, $H_2$, and 0.1 to 10.0 LHSV, preferably 300° to 400° C., 1000 to 1500 psi $H_2$, and 1 to 2 V/V/hr.

The following examples are illustrative of the invention though not limiting.

EXAMPLE 1

The catalysts of the examples were prepared by calcining at 600° C. overnight an amorphous silica-alumina containing 75% silica and 25% alumina. The desired amount of $Nd(NO_3)_3.6H_2O$ was added to 9cc of water (refer to Table I). The neodymium nitrate-containing solution was then impregnated onto 14 grams of the amorphous silica-alumina via the incipient wetness technique. The impregnated support was then dried overnight at 110° C. and calcined between about 500° and 600° C. for three hours. 4.985 g of the support was then impregnated via the incipient wetness technique with a 2.5 cc volume of an aqueous chloroplatinic acid solution containing 0.015 g of platinum followed by drying at 110° C. overnight and calcining at 450° C. for three hours to yield 0.3% Pt on X % $Nd_2O_3$ on $SiO_2$-$Al_2O_3$. As herein used X represents the % of neodymium oxide on the support as described in table I.

TABLE I

| X = desired % $Nd_2O_3$ | Wt (g) $Nd(NO_3)_3.6H_2O$ in 9 cc water |
| --- | --- |
| 10 | 4.1 |
| 12 | 5.0 |
| 14 | 5.9 |
| 17 | 7.5 |

TABLE I-continued

| X = desired % Nd$_2$O$_3$ | Wt (g) Nd(NO$_3$)$_3$.6H$_2$O in 9 cc water |
|---|---|
| 20 | 9.1 |
| 25 | 12.2 |
| 30 | 15.6 |

The acidity of platinum on neodymium oxide modified amorphous silica-alumina catalysts was compared to that of chlorided and fluorided alumina catalysts using the 2-methylpent-2ene (2MP2) acidity probe test. The formation rates and rate ratios of the product hexene isomers of the test reflect the acid site concentration and strength of the catalyst respectively. The product hexene isomers formed include 4-methylpent-2ene (4MP2), t-3-methylpent-2ene (t-3MP2), and 2,3 dimethylbute-2ene (2,3 DMB2). 4MP2 requires only a double bond shift, a reaction occurring on weak acid sites. 3MP2 requires one methyl group shift (i.e., stronger acidity than double bond shift), whereas 2,3DMB2 requires even stronger acidity to produce a second methyl branch. For a homologous series of solid acids, differences in t-3MP2 rates normalized with respect to surface area reflect the density of acid sites possessing strengths sufficient to catalyze the skeletal isomerization. Since skeletal isomerization rates generally increase with increasing acid strength, the ratio of methyl group migration rate to double bond shift rate should increase with increasing acid strength. The use of rate ratios, in lieu of individual conversion rates is preferable since differences in acid site populations are normalized.

The prepared supports as discussed above, prior to platinum impregnation, were compared to chlorided and fluorided alumina catalysts having between 0.6 and 1.5 Wt% chloride and 0.9 and 3.0 Wt% fluoride incorporated, respectively, therein. The % conversion of 2-methylpent-2ene as well as the ratios of t-3MP2/4MP2, 2,3 DMB2/4MP2, and % C$_5$- selectivity were determined. The catalysts were reduced for 1 hour at 500° C. prior to the run. The runs were conducted at 2.5 w/w/hr and 15psia. The following data, in Table II, was obtained after 1 hour on feed. All catalysts were calcined at 600° C. except as otherwise noted. The numbers appearing in front of Nd$_2$O$_3$ indicate the wt % of Nd$_2$O$_3$ present.

TABLE II

| CATALYST | % CONV. | t-3MP2/ 4MP2 | 2,3DMB2/ 4MP2 | % C$_5$— |
|---|---|---|---|---|
| SiO$_2$—Al$_2$O$_3$ | 75 | 2.9 | 0.69 | 1.7 |
| 10Nd$_2$O$_3$/SiO$_2$—Al$_2$O$_3$ | 75 | 2.8 | 0.62 | 2.1 |
| 12Nd$_2$O$_3$/SiO$_2$—Al$_2$O$_3$ | 71 | 2.7 | 0.56 | 1.4 |
| 14Nd$_2$O$_3$/SiO$_2$—Al$_2$O$_3$ | 71 | 2.5 | 0.41 | 1.5 |
| 17Nd$_2$O$_3$/SiO$_2$—Al$_2$O$_3$ | 70 | 2.2 | 0.34 | 1.3 |
| 20Nd$_2$O$_3$/SiO$_2$—Al$_2$O$_3$ | 68 | 2.1 | 0.29 | 1.1 |
| 25Nd$_2$O$_3$/ SiO$_2$—Al$_2$O$_3$ (a) | 47 | 0.47 | 0.056 | 0.17 |
| 25Nd$_2$O$_3$/ SiO$_2$—Al$_2$O$_3$ (b) | 58 | 1.2 | 0.13 | 0.57 |
| 25Nd$_2$O$_3$/ SiO$_2$—Al$_2$O$_3$ (c) | 60 | 1.2 | 0.14 | 0.62 |
| 30Nd$_2$O$_3$/SiO$_2$—Al$_2$O$_3$ | 57 | 1.1 | 0.12 | 0.47 |
| .9Cl/Al$_2$O$_3$ | 30 | 0.14 | 0.071 | 0.04 |
| 1.2Cl/Al$_2$O$_3$ | 33 | 0.25 | 0.36 | 0.05 |
| .9F/Al$_2$O$_3$ | 39 | 1.2 | 0.21 | 0.059 |
| 3.0F/Al$_2$O$_3$ | 74 | 3.7 | 0.91 | 0.63 |

(a) 1st catalyst prep with 500° C. Calcination
(b) 1st catalyst prep with 600° C. calcination
(c) 2nd catalyst prep with 600° C. calcination FIG. 1 graphically depicts the results obtained from the catalysts of Example 1. The + signs depict the first catalyst preparation with calcination at 600° C. at varying neodymium oxide loadings. The x represents a second catalyst preparation having 25% neodymium oxide and calcined at 500° C. The represents a second catalyst preparation having 25% neodymium oxide and calcined at 600° C. The blocks represent fluorided-alumina catalyst having from 0.9 to 3.0% fluoride incorporated therein and chlorided-alumina chloride catalysts having from 0.6 to 1.5% incorporated therein. The ratio of t-3MP2 to 4MP2 was compared to silica-alumina supports having varying amounts of neodymium oxide incorporated therein denoted as x Nd$_2$O$_3$/SiO$_2$.Al$_2$O$_3$ where x represents the amount of neodymium oxide.

The results show that the acidity of amorphous silica-alumina is systematically lowered by the addition of neodymium oxide. Reproducibility is also demonstrated as well as the effect of calcination temperature.

EXAMPLE 2

Figure 2:
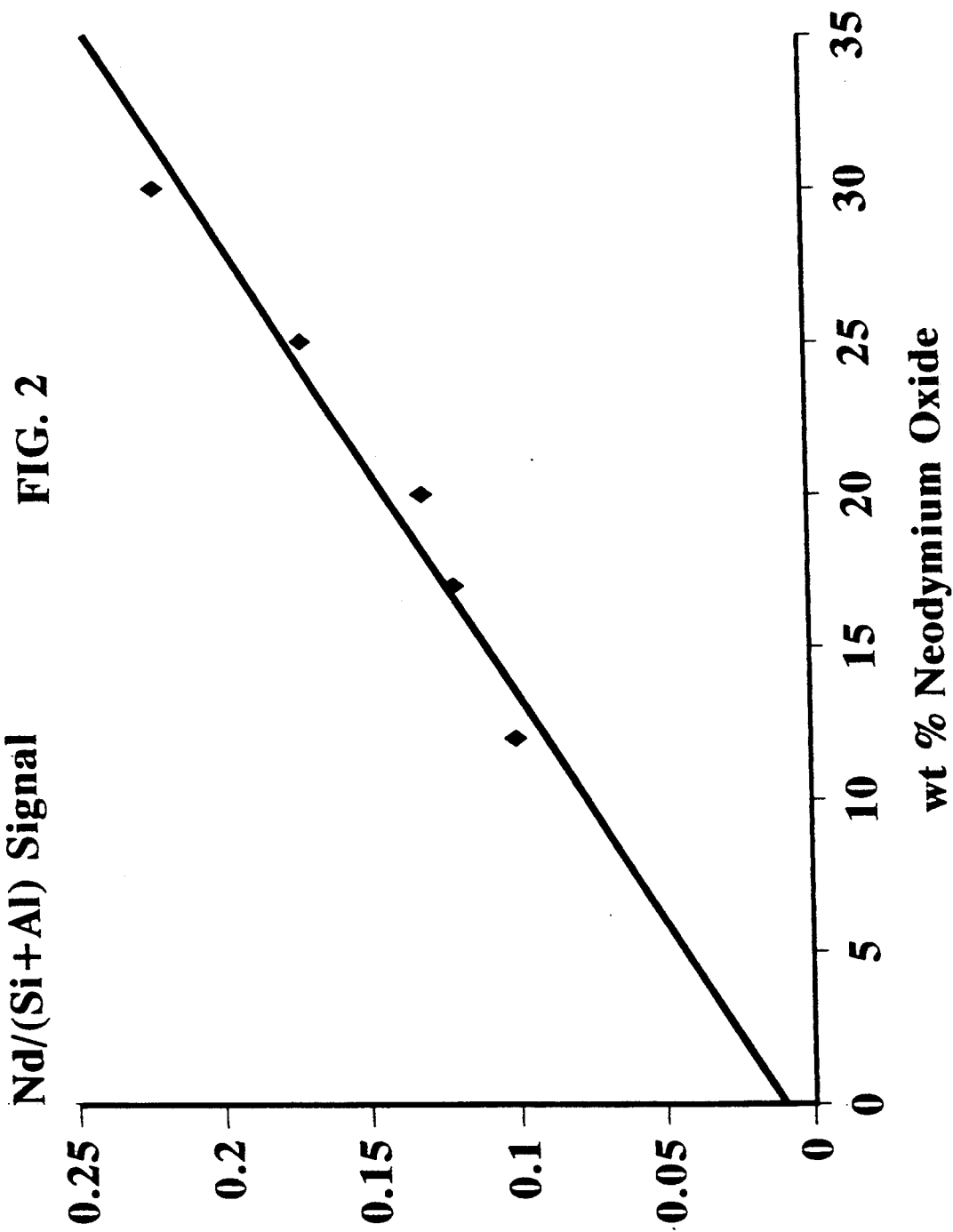
FIG. 2 depicts the monolayer dispersion of neodymium oxide as a function of neodymium oxide loading by measuring the Nd/(Si+Al) signal using the ESCA (electron spectroscopy for chemical analysis) technique.

The same catalysts of Example 1, all calcined at 600° C., prior to having platinum incorporated into the support were analyzed by ESCA. FIG. 2 graphically represents the results.

The ESCA results indicate that the rare earth oxide is evenly dispersed and a monolayer dispersion of the rare earth oxide is present. This demonstrates that there is no agglomeration of the rare earth oxide and that the rare earth oxide evenly and gradually lowers the acidity of the amorphous silica-alumina support.

EXAMPLE 3

The same catalysts of Example 1 calcined at 600° C. prior to platinum impregnation and then impregnated with 0.3 wt% platinum by chloroplatinic acid calcined at 450° C. and then reduced at 450° C. were analyzed for platinum dispersion. The platinum dispersion was measured by H$_2$ chemisorption and the weak adsorption as determined from the backsorption was subtracted from the total adsorption to give only the strongly chemisorbed sites. The results are graphically depicted in FIG. 3.

The results demonstrate that addition of Nd$_2$O$_3$ enhances platinum dispersion on an amorphous silica-alumina catalyst.

EXAMPLE 4

Pt/25%Nd$_2$O$_3$/SiO$_2$.Al$_2$O$_3$, Pt/Cl-Al$_2$O$_3$, and Pt/Si-Al catalysts were compared for n-C$_7$ conversion activities. The reaction was conducted in a fixed bed reactor equipped with a gas chromatograph. The catalyst of the present invention, after platinum impregnation, was calcined in air for 4 hours at 450° C. and reduced at 450° C. The Pt/Cl-Al$_2$O$_3$ catalyst contained 0.3% Pt and 0.9% Cl, the Pt/Si-Al catalyst contained 0.6% Pt. Two catalysts of the present invention were used, the first having 0.3% Pt, and the second having 0.6% Pt incorporated therein. A 50 hour run was conducted.

The Pt/Cl-Al$_2$O$_3$ catalyst showed a steady C$_7$ conversion of about 80% over a period of 50 hours. The Pt/Si-Al catalyst exhibited about an 85% conversion initially, but dropped off after about 8 hours stabilizing around 30 to 40% after about 20 hours and continuing for the entirety of the run. The present invention catalyst having 0.3% Pt incorporated therein began at about a 55% conversion at about 5 hours and stabilized at about 40 to 50% conversion until the run was terminated at about 20 hours. The present invention catalyst having 0.6% Pt incorporated therein began at about a 50% conversion, stabilizing at about 35% for the entirety of the run. The results are graphically depicted in FIG. 4 view A. The solid line connecting the dots represents the chlorided-alumina catalyst containing 0.3% platinum and 0.9% Cl (Pt/Cl-Al$_2$O$_3$), the solid line connecting the larger boxes represents the platinum containing amorphous silica-alumina catalyst having 0.6% platinum and no rare earth oxide (Pt/Si-Al). The solid lines connecting the asterisks and plus signs represent neodymium oxide modified amorphous silica-alumina having 0.3% and 0.6% platinum respectively and each containing 25% neodymium oxide. The present invention catalyst shows higher stability than the Pt/Si-Al catalyst.

EXAMPLE 5

The catalysts of Example 4 were compared for aromatics (benzene and toluene) wt% selectivity over a 50 hour period with the following results:

The Pt/Cl-Al$_2$O$_3$ catalyst showed a % selectivity of about 38% initially and dropped off at about 3 hours stabilizing at about 25% over the remainder of 50 hours. The Pt/Si-Al catalyst showed about a 3% aromatic selectivity for the entirety of the run. The present invention catalyst having 0.3% Pt incorporated therein began at about an 18% selectivity at about 3 hours, and stabilized at about 9 to 10% selectivity up to about 20 hours when the run was terminated. The present invention catalyst having 0.6% Pt incorporated therein began at about an 18% selectivity, stabilizing at about 10% for the entirety of the run. The results are graphically depicted in FIG. 4 view B. The lines represent the catalysts as noted in FIG. 4 view A.

The catalysts were also compared over the 50 hour period for C$_7$ isomer selectivity with the following results:

Both catalysts of the present invention began at about 56% selectivity and rose to about 70% selectivity at about 8 hours. The catalyst having 0.3% Pt therein was terminated at 20 hours. The Pt/Cl-Al$_2$O$_3$ catalyst showed a steady C$_7$ isomer selectivity of about 48%. The Pt/ Si-Al catalyst showed about 18% selectivity. The results are graphically depicted in FIG. 4 view C. The lines represent the catalysts as noted in FIG. 4 view A.

The catalysts were also compared for C$_5$- selectivity. The Pt/Si-Al catalyst showed a C$_5$-selectivity of about 80%, the chlorided catalyst showed a C$_5$-selectivity of about 24%, and the catalysts of the present invention showed about 18% selectivity.

The results demonstrate that the catalysts of the present invention are stable affording better aromatic selectivity and lower cracking than Pt/Si-Al catalysts, but have a lower activity than chlorided catalysts. Neodymium oxide addition reduced cracking relative to Pt/SiO$_2$-Al$_2$O$_3$, and isomerization occurred at the expense of dehydrocyclization compared to chlorided catalysts. The results are graphically depicted in FIG. 4 view D. The lines represent the catalysts as noted in FIG. 4 view A.

What is claimed is:

1. A catalyst composition comprising an amorphous silica-alumina support having at least about 50 wt% silica, a rare earth oxide, and metal(s) selected from the group consisting of Group VIII noble metal(s), mixtures of Group VIII noble metal(s) and rhenium and mixtures of Group VIII noble metal(s) and tin.

2. A catalyst composition according to claim 1 wherein said rare earth oxide is present in an amount of about 1 to about 90 weight percent.

3. A catalyst composition according to claim 1 wherein said rare earth oxide is present as a monolayer dispersed on the surface of said amorphous silica-alumina.

4. A catalyst composition according to claim 2 wherein said rare earth oxide is preferably selected from neodymium oxide, yttrium oxide and mixtures thereof.

5. A catalyst composition according to claim 1 wherein said Group VIII noble metal is present in an amount of about 0.01 to about 10 weight percent.

6. A catalyst composition according to claim 1 wherein said silica-alumina support has a ratio of silica:alumina of about 50:50 to about 95:5.

7. A catalyst composition according to claim 1 wherein said Group VIII noble metal is selected from the group consisting of platinum, iridium, rhodium, palladium, ruthenium and mixtures thereof.

8. A catalyst composition according to claim 1 wherein said Group VIII noble metal is platinum.

* * * * *